United States Patent [19]

Wildman et al.

[11] 4,268,632

[45] May 19, 1981

[54] PROCESS FOR ISOLATION OF RIBULOSE 1,5-DIPHOSPHATE CARBOXYLASE FROM PLANT LEAVES

[75] Inventors: Samuel G. Wildman, Santa Monica; Prachuab Kwanyuen, Los Angeles, both of Calif.

[73] Assignee: Leaf Proteins, Inc., Carson, Calif.

[21] Appl. No.: 78,505

[22] Filed: Sep. 24, 1979

[51] Int. Cl.$^3$ ............................................. C12N 9/88
[52] U.S. Cl. .................................. 435/232; 435/814; 435/816
[58] Field of Search .......................................... 435/232

[56] References Cited

PUBLICATIONS

Barman, Enzyme Handbook, vol. II, pp. 723–724 (1969).

Kawishima et al., Biochimica Biophysica Acta, vol. 229, pp. 749–760 (1971).

*Primary Examiner*—Lionel M. Shapiro
*Attorney, Agent, or Firm*—Lyon & Lyon

[57] ABSTRACT

Described herein is a process for isolating the enzymatic protein ribulose 1,5-diphosphate carboxylase from the green leaves of plants. In the process, which is particularly suited to obtaining the protein from tobacco, the leaves are ground or otherwise pulverized in the presence of a reducing agent, followed by heating the resulting pulp to about 50° C. A liquid portion containing the desired protein is separated from the pulp and then cooled to cause the crystallization of the ribulose 1,5-diphosphate carboxylase. After separation of the crystalline material, the supernatant is acidified to yield lower molecular weight proteins.

27 Claims, No Drawings

PROCESS FOR ISOLATION OF RIBULOSE 1,5-DIPHOSPHATE CARBOXYLASE FROM PLANT LEAVES

FIELD OF THE INVENTION

In a broad aspect this invention relates to a process for isolating proteins from plant leaves. In another aspect it relates to a process for obtaining ribulose 1,5-diphosphate carboxylase from the green leaves of plants. In another, and more specific aspect, it relates to a process for obtaining ribulose 1,5-diphosphate carboxylase from tobacco leaves.

BACKGROUND

The succulent leaves of certain plants, including tobacco, spinach, soybeans, wheat, cotton and alfalfa, are composed of 10-20% solids, the balance being water. For its part, the solid portion is composed of a water soluble portion and a water insoluble portion, the latter being made up, for the most part, of the fibrous structural material of the leaf.

The water soluble compounds are divisible into two groups. One group includes compounds of relatively lower molecular weight such as sugars, vitamins, amino acids and other compounds whose molecular weight do not exceed about 10,000. The second group is almost exclusively proteins whose molecular weight are about 30,000 or greater.

The proteins can be resolved into two fractions. One fraction contains a mixture of proteins whose molecular weight range from about 30,000 to 100,000. These proteins are sometimes referred to as "Fraction 2 proteins." The remaining fraction comprises a single protein having a molecular weight of about 550,000 and is sometimes referred to as "Fraction 1 protein."

Fraction 1 protein was first identified in 1947. Subsequent research led to the discovery that this protein was an enzyme involved in photosynthesis. Since then it has been given a number of names. Among these are ribulose 1,5-diphosphate carboxylase, carboxydismutase, ribulose 1,5-biphosphate carboxylase and ribulose 1,5-di(or bis) phosphate carboxylase-oxygenase.

Fraction 1 protein may compose up to 25% of the total protein content of a leaf and up to 10% of the solid matter in the leaf. In 1970 it was discovered that crystalline Fraction 1 protein could be obtained from tobacco leaves.

Fraction 1 protein, when pure, is odorless, tasteless and colorless and has high nutritional value. In view of these properties, and because it can be obtained in high purity, Fraction 1 protein is considered to have a potentially valuable application as a food supplement for animals and humans. In the case of humans, the additive could be a component of high protein or other special diets. It has, for example, been suggested as a supplement to the diet of persons who require dialysis because of kidney disease.

Despite its relative abundance in cultivated plants, Fraction 1 protein is not a commercially important product since the processes known to the art for obtaining it from vegetable matter are not commercially feasible.

Three basic processes for isolating Fraction 1 protein have been described in the published literature. Each published method begins with pulping the leaves, or leaves and stalk of the plant, followed by expressing a green juice from the pulp. The green juice, which contains finely particulate green pigmented material, is clarified for example, by filtration or centrifugation, to separate the finely particulate solid matter from the liquid. The resulting liquid is brown in color.

The first method described for isolating Fraction 1 protein involved concentration of Fraction 1 protein simultaneously with its partial separation from lower molecular weight compounds in the brown juice by molecular filtration. Using a molecular sieve whose pores would pass smaller molecules without passing Fraction 1 protein, the brown juice was placed under pressure so that small molecules would pass through the pores.

The solution containing the Fraction 1 protein was concentrated about ten-fold and then dialyzed to remove additional small molecules in the solution. Dialysis was accomplished using a collodion type dialysis bag. The pores of the bag would not permit passage of the Fraction 1 protein but allowed the smaller molecules to escape through the bag into water. During dialysis, crystals of Fraction 1 protein formed.

The second method developed to isolate the Fraction 1 protein involved passing the brown juice obtained from the leaves through a Sephadex chromatographic column. Sephadex consists of water insoluble microscopic beads of polymerized sugar. Either Sephadex G-25 or G-50 was used to perform the separation. Selection of proper beads permits small molecules to penetrate to the interior of their structure to the exclusion of larger molecules. The larger molecules, therefore, are only found in the liquid in the interstices between the tightly packed Sephadex beads. This interstitial space is referred to as the "void volume".

To achieve effective separation, the volume of brown juice cannot exceed about 25% of the total volume of the beads. The beads are first equilibrated with a buffer and a volume of brown juice, containing the same buffer, is then layered on top of the Sephadex column.

The brown liquid is eluted from the column using the buffer solution. As the juice moves down the column, the passage of small molecules is retarded since they penetrate the interior of the beads. The large Fraction 1 molecules, on the other hand, move at a faster rate down the column through the Labyrinth formed by the interstices between the beads and emerges from the column as a clear brown solution. However, elution results in at least two-fold dilution of the solution. Removal of the smaller molecules changes the environment around the molecules of Fraction 1 protein which leads to crystallization.

The most recently described method provides passage of the brown juice through a Sephadex G-25 column as described above. If Fraction 1 protein does not crystallize, as is the case with the extract of all plants except tobacco, ammonium sulfate is added until the solution is 30-50% saturated. This leads to precipitation of an amorphous material which is collected by centrifugation. After separation, the precipitate is redissolved in a smaller volume of buffer than that from which it was precipitated to which is added 8% polyethylene glycol. This mixture is placed in an open dish adjacent to another open dish containing silica gel and the two dishes confined in a closed vessel. Water is gradually evaporated from the protein solution and absorbed by the silica gel. With the passage of time, crystals of Fraction 1 protein develop.

It will be clear to those skilled in the art that the prior art process described above are either time consuming, expensive or both.

In view of the potential it has as a food supplement, the shortcomings of the processes known to the art for isolating Fraction 1 protein has revealed the importance of developing an improved process for this purpose. Accordingly, an object of this invention is to provide an improved process for isolating Fraction 1 protein.

Another object of this invention is to obtain Fraction 1 protein in high yield and in high purity.

That these and other objects may be accomplished by the present invention will be apparent to those skilled in the art from the following summary and detailed description of the invention.

SUMMARY OF THE INVENTION

The present invention provides an improved process for isolating ribulose 1,5-diphosphate carboxylase from the leaves of green plants. In that regard, we have discovered, that, after the leaves have been converted to a pulp by grinding or other suitable treatment, unexpectedly ribulose, 1,5-diphosphate carboxylase can be induced to crystallize directly from the liquid portion of the pulp in high yield and high purity by first heating the liquid portion of the pulp, but at a temperature below that which denatures the protein causing it to precipitate as an insoluble mass, followed by cooling the liquid to a temperature at which crystals of ribulose 1,5-diphosphate form, usually at or below room temperature.

DETAILED DESCRIPTION OF THE INVENTION

The process of the present invention can be used to isolate ribulose 1,5-diphosphate carboxylase and lower molecular weight protein from leaves of many varieties. However, because tobacco leaves, and particularly the leaves of immature tobacco, are a particularly rich source of the protein, it is preferred to use such leaves in the process of the invention. Accordingly, the invention will be described with specific reference to the isolation of ribulose 1,5-diphosphate carboxylase from tobacco.

After detachment of the leaves from the tobacco plant, the leaves, or leaves and stalk together if small plants are the source of the leaves, are ground, crushed or otherwise reduced to a pulp to release the liquid portion of the leaves from the solids. Preferably, the pulping process is carried out in the presence of a reducing agent. In that regard, the pulping process permits phenol oxidase enzymes present in the leaves to contact the leaf proteins. This results in oxidation of aromatic amino acids such as tyrosine which comprise part of the primary structure of proteins. This oxidation modifies the protein, made visually manifest by their becoming brown, and lowers their solubility in water. The reducing agent, in effect, acts as an antioxidant to suppress this oxidation.

The presently preferred reducing agent for use in the invention is 2-mercaptoethanol because it is volatile and evaporates during the further processing described below leaving little or no residue in the material isolated. However, other reducing agents may also be used. Among these are agents such as sodium metabisulfite and dithiothreitol. Separation of the residue of these agents, if any, can be done using conventional techniques. The amount of reducing agent sufficient to control the oxidation can vary depending, for example, on the agent selected. In the case of 2-mercaptoethanol, effective suppression of the undesirable oxidation can be achieved using about 5 milliliters of the liquid agent per kilogram of plant material being processed.

The liquid portion of the plant material contains the plant proteins in dissolved form. As indicated above, we have found that, unexpectedly, heat treatment of the liquid portion of the pulp containing the ribulose 1,5-diphosphate carboxylase followed by cooling induces this protein to crystallize from the liquid. The mechanism by which the heat treatment induces crystallization is not clear. However, while applicants do not wish to be bound by any theory, it is believed that the heat treatment modifies the protein in some way that favors crystallization. In that regard, three crystalline forms of Fraction 1 protein crystals have been described in the published literature. Form I crystals have the shape of dodecahedrons and are produced by the previously mentioned processes using molecular sieves or Sephadex chromatography. Form II crystals have the shape of extremely thin plates and so far have been produced only under very special conditions and in extremely small amounts for X-ray crystallographic studies. Form III crystals are tetragonal bipyramids and are produced by the ammonium sulfate and polyethylene glycol treatment previously mentioned.

By contrast, the Fraction 1 protein crystals produced by the process described herein take yet a fourth form, unlike the other three forms of crystals known to the art. Thus, using the process of the present invention, Fraction 1 protein crystals are obtained having an apparent octagonal form, by microscopic examination, in high yield and in high purity.

In contrast to Form I crystals which will redissolve in water containing common salt (NaCl), the octagonal crystals remain undissolved but will go into solution when the crystals are suspended in water adjusted to pH 7.5 by sodium hydroxide (NaOH). Dialysis of the redissolved Fraction 1 protein against distilled water will cause recrystallization, but now as Form I crystals.

The solid matter in the pulp includes coarse, easily separated material and finely particulate green pigmented material which is difficult to separate from the liquid. However, the heat treatment of this invention, the details of which will be described below, in addition to inducing crystallization of the Fraction 1 protein also causes partial coagulation of the pigmented material which facilitates its removal during further processing. For example, the material can be removed by moderate centrifugal force. Therefore, the heat treatment is applied to the liquid portion prior to separation of the liquid portion from the coarse solid material. Heating of the entire pulp, i.e., prior to removal of any solid material, is preferred because we have found that better yields of the crystalline ribulose 1,5-diphosphate carboxylase are obtained in this way than if heating is performed after removal of the coarse material but prior to removal of the pigmented material.

The heating step is carried out at a temperature and for a time sufficient to induce crystallization of ribulose, 1,5-diphosphate carboxylase, as octagonal crystals, from the liquid portion of the pulp when the liquid is cooled. However, in no instance, should the liquid portion be heated in excess of the temperature at which the protein denatures, about 52° C., and precipitates immediately as in insoluble means.

Although lower temperatures than 52° C. may be used, it is preferred to use a temperature of at least about 48° C. as below that temperature the green pigmented materials do not coagulate sufficiently to permit their easy removal. Furthermore, below 48° C. the heating time required to induce the crystallization of ribulose 1,5-diphosphate carboxylase may be inconveniently long. Best results are obtained by heating the liquid portion to 50°±1° C. for from about 15 to about 20 minutes.

The passage of time between harvesting the leaves, converting them to a pulp and heating the pulp as described above reduces the yield of the crystalline ribulose 1,5-diphosphate carboxylase which can be achieved by the process of the present invention. Therefore, these steps should be delayed for as short a time as possible. To that end, it is preferred to perform these operations in or near the site of cultivation as the leaves are harvested.

Conversion of the leaves to a pulp can be by grinding, crushing or any other suitable process.

The heat treatment can be performed either as a continuous or batch process. In a batch process, the pulp is placed in a vessel whereby heat is transferred to the pulp under conditions where no part of the pulp, or at least the liquid portion thereof, is heated to a temperature at which the protein denatures. As indicated above, preferably the pulp is heated to a temperature of 50°±1° C. for from about 15 minutes to about 20 minutes.

In a continuous process, the pulp is pumped without undue agitation through coils immersed in a liquid heated to a temperature such that, by heat exchange, a specified volume of pulp would be heated to 50°±1° C. for from about 15 minutes to about 20 minutes and then through coils in contact with liquid at a temperature lower than 50° C. to reduce the temperature of the pulp.

After having been heated, the liquid and solid portions of the pulp are separated. Separation is conveniently accomplished by first pressing the pulp to express the liquid portion therefrom. The liquid obtained in this way is a "green juice" containing the green pigmented material. When heated above about 48° C. to cause its coagulation, this material is simply removed, for example, by filtration or moderate centrifugation, to yield a "brown juice".

To obtain the ribulose 1,5-diphosphate carboxylase, the brown juice is cooled to and stored at a temperature at which crystallization will occur, usually at or below room temperature. Particularly good results have been obtained by cooling the brown juice to about 8° C. for about 24 hours. The crystallized ribulose 1,5-diphosphate is separated from the supernatant liquid by filtration or centrifugation.

The supernatant liquid contains Fraction 2 proteins and a portion of uncrystallized Fraction 1 protein. These proteins may be recovered by acidifying the supernatant liquid which causes their precipitation. Best results are obtained by acidification to a pH of about 4.5. Less protein is precipitated if a pH of 4.0 or pH 5.0 is employed.

The foregoing description of the invention has stressed the process in which the entire pulp is heated prior to separation of the liquid portion. However, as previously indicated, the heating step can be carried out after the liquid portion containing a suspension of the green pigmented materials is separated from the pulp. Further details of the invention will become apparent from consideration of the following example.

EXAMPLE

Type NC95 tobacco plants are cultivated at a plant density of 0.5 square feet per plant until a height of 18-24 inches is attained. The plants are cultivated in such a way that the leaves are deep green in color. The entire aerial portions of the plants are harvested and cut into pieces small enough to be introduced into a one gallon size Waring blender. The blades of the blender are covered with about 200 ml. of water. (The Waring blender will not disintegrate the plant material unless the blades are submerged in a liquid. However, with other such devices, such as a Rietz disintegrator, addition of water would be unnecessary).

A one kilogram batch of coarsely chopped stems and leaves obtained from the harvested plant material is added to the water with 5 ml. of 2-mercaptoethanol and blended to a smooth pulp. The resulting pulp, which has the consistency of a thick pancake batter, consisting of a volume of about 1.2 liters, is divided into 400 ml. portions, each portion contained in a 1-liter erlenmeyer flask. The pulp is heated by submerging the erlenmeyers in a water bath at 50°±0.1° C. for about 15 minutes. The heated pulp is then cooled to ambient temperature by pouring it onto two layers of 24/20 mesh cheesecloth supported on an 8 inch diameter, 32 mesh sieve which is placed in a large funnel draining into a collecting flask. Separation of the liquid from the heated pulp should be done promptly, i.e., within 2 hours, to avoid serious reduction in yield of ribulose 1,5-diphosphate carboxylase.

Processed in this way, the 1.2 liters of pulp yields approximately 1.1 liter of liquid containing green pigmented material. The "green juice" is subjected to sufficient centrifugal force to produce a precipitated green sediment in a brown supernatant liquid. Centrifuging for 30 minutes at 5000 rpm in a GSA type rotor in a Servall centrifuge is adequate for this purpose. In this way approximately 0.1 kilogram of green sediment is obtained.

Separation of the supernatant from the precipitated sediment yields about 1 liter of brown liquid. After 24 hours at about 8° C., crystals of ribulose 1,5-diphosphate carboxylase as apparent octagonal crystals.

After separation of the crystalline ribulose 1,5-diphosphate carboxylase, addition of hydrochloric acid to the brown supernatant to adjust its pH to 4.5 causes rapid precipitation of Fraction 2 proteins and uncrystallized Fraction 1 protein. Approximately 5 grams of material is obtained in this way. At pH 4.0, 18% less protein is precipitated and at pH 5.0, 16% less protein is precipitated than is precipitated at pH 4.5.

From the foregoing description, it can be seen that the present invention provides a convenient process for obtaining protein, and especially Fraction 1 protein, from plant material. Thus, the process of the present invention obviates the need for costly and elaborate molecular filtration and Sephadex columns as required by prior art processes. Furthermore, no chemical agent is required other than the reducing agent which, in the case of 2-mercaptoethanol, is driven off in the heating step, in order to obtain the Fraction 1 protein. Furthermore, because it is unnecessary to dilute the liquid, recovery of Fraction 2 proteins is also simplified. Finally, after removal of the Fraction 2 proteins and uncrystallized Fraction 1 protein from the liquid portion, the liquid portion still contains low molecular weight compounds of value that can be more economically recovered than would be the case using the residue obtained by prior art processes since they are in their natural form and undiluted. By contrast, the residues obtained from prior art processes are contaminated by the chemicals used in the process and have been diluted during separation of the Fraction 1 protein which complicates further recovery.

The invention has been described in terms of presently preferred embodiments. However, from the foregoing description of the invention, those skilled in the art will appreciate that modifications of the process can be made without departing from the scope of the invention which is to be limited only by the appended claims.

We claim:

1. A process for obtaining ribulose 1,5-diphosphate carboxylase from plant material comprising the leaves of green plants comprising the steps:
   (a) converting the leaves to a pulp comprising a mixture of a solid portion and a liquid portion, said liquid portion containing dissolved ribulose 1,5-diphosphate carboxyase;
   (b) heating the liquid portion to a temperature below that at which protein in the liquid portion denatures for a time sufficient to induce the ribulose 1,5-diphosphate carboxylase to crystallize when said liquid portion is cooled; and
   (c) cooling said liquid portion to a temperature at which said ribulose 1,5-diphosphate carboxylase crystallizes.

2. A process according to claim 1 wherein the liquid portion is heated prior to its separation from the solid portion of the pulp.

3. A process according to claim 2 wherein said heating is at a temperature of from about 48° C. to about 52° C.

4. A process according to claim 3 wherein said liquid portion is cooled to a temperature at or below room temperature after said heating.

5. A process according to claim 1 wherein the liquid portion and suspended green pigmented material is separated from said pulp prior to said liquid portion being heated.

6. A process according to claim 5 wherein said heating is at a temperature of from about 48° C. to about 52° C.

7. A process according to claim 6 wherein said green pigmented material is separated from said liquid portion after heating of the liquid portion.

8. A process according to claim 7 wherein said liquid portion is cooled to a temperature at or below room temperature after said heating.

9. A process according to claim 1 wherein conversion of said leaves to a pulp is accomplished in the presence of a reducing agent, said reducing agent being employed in an amount sufficient to suppress oxidation of amino acid substituent groups comprising part of the structure of proteins present in said liquid portion.

10. A process according to claim 9 wherein said reducing agent is 2-mercaptoethanol.

11. A process according to claims 1, 2, 3, 4, 5, 6, 7, 8, 9 or 10 wherein said ribulose 1,5-diphosphate carboxylase crystallizes as octagonal crystals.

12. A process according to any of claims 1, 2, 3, 4, 5, 6, 7, 8, 9 or 10 comprising the additional steps of separating the crystallized ribulose 1,5-diphosphate carboxylase from said liquid portion and acidifying said liquid portion to precipitate Fraction 2 protein.

13. Ribulose 1,5-diphosphate carboxylase in the form of octagonal crystals.

14. A process according to claims 1, 2, 3, 4, 5, 6, 7, 8, 9, or 10 wherein the leaves are tobacco leaves.

15. A process according to claims 1, 2, 3, 4, 5, 6, 7, 8, 9, or 10 wherein the leaves are tobacco leaves and wherein said ribulose 1,5-diphosphate carboxylase crystallizes as octagonal crystals.

16. A process according to claims 1, 2, 3, 4, 5, 6, 7, 8, 9, or 10 wherein the leaves are tobacco leaves, said ribulose 1,5-diphosphate carboxylase crystallizes as octagonal crystals and wherein the process comprises the additional steps of separating the crystallized ribulose 1,5-diphosphate carboxylase from said liquid portion and acidifying said liquid portion to precipitate Fraction 2 protein.

17. A process for obtaining ribulose 1,5-diphosphate carboxylase from tobacco plant material comprising the steps:
   (a) converting the plant material to a pulp comprising a mixture of a solid portion and a liquid portion, the liquid portion containing dissolved ribulose 1,5-diphosphate carboxylase;
   (b) heating the pulp to a temperature below that at which the protein in the liquid portion denatures for a time sufficient to induce the ribulose 1,5-diphosphate carboxylase to crystallize when said liquid portion is cooled;
   (c) separating the liquid portion from the solid portion; and
   (d) cooling the liquid portion to a temperature at which said ribulose 1,5-diphosphate crystallizes.

18. A process according to claim 17 wherein the pulp is heated to a temperature from about 48° C. to about 52° C.

19. A process according to claim 17 wherein said plant material comprises the leaves of said tobacco.

20. A process according to claim 19 wherein said plant material comprises the leaves and stalk of said tobacco.

21. A process according to claim 19 wherein the pulp is heated to a temperature from about 48° C. to about 52° C.

22. A process according to claim 20 wherein the pulp is heated to a temperature from about 48° C. to about 52° C.

23. A process according to claim 17 wherein a reducing agent is added to said plant material in an amount sufficient to suppress oxidation of amino acid substituent groups comprising part of the structure of proteins present in said liquid portion.

24. A process according to claim 23 wherein said reducing agent is 2-mercaptoethanol.

25. A process according to claim 23 wherein said reducing agent is added to the plant material prior to its conversion to said pulp.

26. A process according to claims 23, 24 or 25 wherein the plant material comprises the leaves of said tobacco and wherein the pulp is heated to a temperature from about 48° C. to about 52° C.

27. A process according to claims 17, 18, 19, 20, 21, 22, 23, 24 or 25 wherein said ribulose 1,5-diphosphate carboxylase precipitates as octagonal crystals.

* * * * *